US008084419B2

(12) United States Patent
Gefter

(10) Patent No.: US 8,084,419 B2
(45) Date of Patent: Dec. 27, 2011

(54) PHARMACEUTICAL COMPOSITIONS FOR SUSTAINED DRUG DELIVERY

(75) Inventor: Malcolm L. Gefter, Lincoln, MA (US)

(73) Assignee: GlaxoSmithKline, LLC, Philadelphia, PA (US)

(*) Notice: Subject to any disclaimer, the term of this patent is extended or adjusted under 35 U.S.C. 154(b) by 594 days.

(21) Appl. No.: 11/173,901

(22) Filed: Jun. 30, 2005

(65) Prior Publication Data

US 2006/0094662 A1 May 4, 2006

Related U.S. Application Data

(63) Continuation of application No. 09/953,247, filed on Sep. 13, 2001, now Pat. No. 7,037,889.

(60) Provisional application No. 60/232,188, filed on Sep. 13, 2000.

(51) Int. Cl.
*A61K 38/09* (2006.01)

(52) U.S. Cl. ....... 514/5.9; 514/10.3; 514/10.7; 514/10.8

(58) Field of Classification Search ........................ None
See application file for complete search history.

(56) References Cited

U.S. PATENT DOCUMENTS

| | | | | |
|---|---|---|---|---|
| 4,489,065 | A | 12/1984 | Walton et al. | |
| 4,980,150 | A | 12/1990 | Keith | |
| 5,744,166 | A | 4/1998 | Illum | |
| 5,747,641 | A | 5/1998 | Frankel et al. | |
| 5,763,422 | A | 6/1998 | Lichtenberger et al. | |
| 5,804,604 | A | 9/1998 | Frankel et al. | |
| 5,830,883 | A | 11/1998 | Block et al. | |
| 5,834,598 | A * | 11/1998 | Lowman et al. | 530/399 |
| 5,846,743 | A | 12/1998 | Janmey et al. | |
| 5,888,762 | A | 3/1999 | Joliot et al. | |
| 5,900,408 | A | 5/1999 | Block et al. | |
| 5,968,895 | A * | 10/1999 | Gefter et al. | 514/2 |
| 5,972,326 | A | 10/1999 | Galin et al. | |
| 6,015,787 | A | 1/2000 | Potter et al. | |
| 6,054,555 | A | 4/2000 | Engel et al. | |
| 6,180,608 | B1 | 1/2001 | Gefter et al. | |
| 6,328,979 | B1 | 12/2001 | Yamashita et al. | |
| 6,699,833 | B1 * | 3/2004 | Gefter et al. | 514/2 |
| 7,037,889 | B2 * | 5/2006 | Gefter | 514/2 |
| 2002/0086829 | A1 * | 7/2002 | Gefter | 514/12 |

FOREIGN PATENT DOCUMENTS

| | | | |
|---|---|---|---|
| CA | 1053581 | A1 | 5/1979 |
| WO | WO-96/39160 | A1 | 12/1996 |
| WO | WO-98/25642 | A2 | 6/1998 |
| WO | WO-99/10376 | A1 | 3/1999 |
| WO | WO-99/29721 | A1 | 6/1999 |
| WO | WO-99/55899 | A1 | 11/1999 |

OTHER PUBLICATIONS

Mezö, G., et al, "Carrier Design: Conformational Studies of Amino Acid (X) and Oligopeptide (X-DL-Ala*m*) Substituted Poly (L-Lysine)," *Biopolymers*, vol. 33(6):873-885 (1993).

Mezö, G., et al., "Synthesis, Conformationa, Biodistribution, and Hormone-Related in Vitro Antitumor Activity of a Gonadotropin-Releasing Hormone Against-Branched Polypeptide Conjugate," *Bioconjugate Chemistry*, vol. 7(6):642-650 (1996).

Ryser, H.J.-P., et al., "Conjugation of Methotrexate to Poly (L-Lysine) as a Potential Way to Overcome Drug Resistance," *Cancer*, vol. 45 (5 Suppl.):1207-1211 (1980).

Citro, G., et al., "Chemical Modification of Ligands for Cell Receptors to Introduce Foreign Compounds into the Cells," *Dis. Colon Rectum*, vol. 37(Suppl.):S127-S132 (1994).

Lali, A., et al., "Carboxymethyl cellulose as a new heterobifunctional ligand carrier for affinity precipitation of proteins," *Bioseparation*, vol. 7:195-205 (1999).

* cited by examiner

*Primary Examiner* — Christopher R. Tate
*Assistant Examiner* — Roy Teller
(74) *Attorney, Agent, or Firm* — McCarter & English, LLP; Maria Laccotripe Zacharakis; Deborah L. Nagle

(57) ABSTRACT

Sustained delivery formulations comprising a water-insoluble complex of a peptide and a plurality of ligands are disclosed. The formulations of the invention allow for loading of high concentrations of peptide in a small volume and for delivery of a pharmaceutically active peptide for prolonged periods, e.g., one month, after administration of the complex. The complexes of the invention can be milled or crushed to a fine powder. In powdered form, the complexes form stable aqueous suspensions and dispersions, suitable for injection. Methods of making the complexes of the invention, and methods of these complexes are also disclosed.

22 Claims, 2 Drawing Sheets

PHARMACEUTICAL COMPOSITIONS FOR SUSTAINED DRUG DELIVERY

RELATED APPLICATIONS

This application is a continuation application of U.S. application Ser. No. 09/953,247, filed Sep. 13, 2001, now U.S. Pat. No. 7,037,889, issued on May 2, 2006, which claims priority to U.S. Provisional Application No. 60/232,188, filed on Sep. 13, 2000. The entire contents of each of the foregoing applications are incorporated herein by this reference.

BACKGROUND OF THE INVENTION

Sustained release systems have been developed over the past several years based on a broad range of technologies, directed to the delivery of a wide selection of pharmaceutical agents. The physical formats for such systems include use of microparticles, slabs or similar macroscopic systems designed for implantation, gels and emulsions, and other preparations conceived to preserve the active agent in the delivery system for an extended period of time.

The mechanism of release for matrix-type sustained release systems is generally understood to occur by hindered diffusion of the active agent through the carrier matrix, or by erosion of the matrix over time resulting in the liberation of the incorporated active agent. These processes are not mutually exclusive, and both mechanisms may be simultaneously active in the case of a given system.

In recent years sustained release devices have been used for the delivery of protein pharmaceutical agents, primarily as a result of the availability of recombinant proteins which have been developed for therapeutic applications in a wide variety of pathological conditions. Development of such systems creates greater challenges to overcome than in the case of low molecular weight drugs and pharmaceutically active substances, since proteins inherently have only marginal conformational stability, and can frequently be susceptible to conditions or processes which result in inactivation or denaturation. In contrast to the degradation or deterioration of low molecular weight pharmaceuticals, the structural alterations in proteins leading to inactivation need not involve changes in the covalent structure of the protein, but can be entirely the consequence of a disruption of an extensive system of non-covalent interactions and/or a disruption of disulfide bonds which are responsible of the preservation of the native three dimensional structure of the protein. This greater lability of proteins, as compared to low molecular weight drugs and other pharmaceutically active substances, creates the need for formulations able to deliver active peptides/proteins in vivo continuously for prolonged time periods.

SUMMARY OF THE INVENTION

The present invention provides compositions comprising a solid, e.g., preferably water insoluble, complex comprising a peptide, preferably a pharmaceutically active peptide, and a plurality of ligands for the peptide, that allow for sustained delivery of the peptide in vivo upon administration of the complex. Accordingly, the composition of the present invention can permit continuous delivery of a peptide to a subject for prolonged periods of time, e.g., one week or one month. Moreover, the association of the peptide and the plurality of ligands in a tight, stable complex allows for loading of high concentrations of the peptide into the composition.

Accordingly, the invention features a composition which includes a plurality of peptide molecules and a plurality of ligands for the peptide, the plurality of ligands being linked; wherein the peptide and the plurality of ligands together form a water insoluble complex. Each of the ligands may be a peptidic or a non-peptidic compound. The complex may be in the form of a solid (e.g., a paste, granules, a powder, or a lyophilizate) or the powdered form of the complex can be pulverized finely enough to form stable liquid suspensions or semi-solid dispersions.

In one embodiment, the plurality of ligands (or sub-combinations thereof, e.g., two, three, or four ligands) are linked directly, e.g., covalently, via electrostatic interactions, via hydrophobic interactions, or a combination thereof. In another embodiment, the plurality of ligands are linked via a carrier macromolecule or via a cross-linking agent. The plurality of ligands (or sub-combinations thereof) may be attached to the carrier macromolecule or the cross-linking agent covalently, via electrostatic interactions, via hydrophobic interactions, or a combination thereof.

In one embodiment, the peptide is selected from the group consisting of insulin, erythropoietin (EPO), growth hormone, bradykinin, parathyroid hormone, adenocorticotrophic hormone, calcitonin, vasopressin, angiotensin, desmopressin, luteinizing hormone-releasing hormone, somatostatin, glucagon, somatomedin, oxytocin, gastrin, secretin, melanocyte stimulating hormone, beta-endorphin, enkephalin, neurotensin, thyroid releasing hormone, macrophage stimulating factor, CCR-5, growth hormone releasing factor (GRF), RGD, tumor necrosis factor (TNF), interleukins (or other cytokines) or peptide mimetics thereof. In another embodiment, the peptide is an LHRH analogue, e.g., an LHRH antagonist having the structure Ac-D-Nal-4-Cl-D-Phe-D-Pal-Ser-N-Me-Tyr-D-Asn-Leu-Lys(iPr)-Pro-D-Ala, the LHRH agonist Leuprolide having the structure pGlu-His-Trp-Ser-Tyr-D-Leu-Leu-Arg-Pro(ethylamide)-Gly, or the LHRH antagonist Cetrorelix having the structure Ac-D-Nal-4-Cl-D-Phe-D-Pal-Ser-Tyr-D-Cit-Leu-Arg-Pro-D-Ala.

In a preferred embodiment, the composition provides sustained delivery of the peptide to a subject for at least one week, two weeks, three weeks, four weeks, five weeks, or more, after the composition is administered to the subject.

In another aspect, the present invention features a composition which includes a peptide; a plurality of ligands for the peptide, each of the ligands being negatively or positively charged; and an ionic carrier macromolecule having an electrical charge opposite to the charge of each of the ligands; wherein the plurality of ligands are linked via the macromolecule and wherein the peptide, the plurality of ligands, and the carrier macromolecule together form a water insoluble complex. Each of the ligands may be a peptidic or a non-peptidic compound. In a preferred embodiment, each of the ligands is a peptidic molecule and each of the ligands comprises an amino acid sequence bearing a net electronic charge, e.g., a positive or a negative charge.

In one embodiment, each of the ligands is cationic and the carrier macromolecule is anionic e.g., an anionic polyalcohol derivative or fragment thereof, an anionic polysaccharide derivative or fragment thereof, an anionic poly-amino acid, alginic acid or a salt thereof, polyglucoronic acid or salt thereof, carrageenan, poly(acrylate), poly(methylacrylate), or starch glycolate.

In another embodiment, each of the ligands is anionic and the carrier macromolecule is cationic, e.g., poly-L-lysine; poly-L-arginine; a poly(allylamine); a poly(vinylamine); a poly(ethyleneimine); an N-alkylated, poly(allylamine); an N-alkylated poly(vinylamine); an N-alkylated poly(ethyleneimine); diethylaminoethyl dextran; diethylaminoethyl cellulose; or poly(d-glucosamine).

In yet another aspect, the invention features a composition which includes a peptide; a plurality of ligands for the peptide, each of the ligands being positively charged, and carboxymethylcellulose; wherein the plurality of ligands are linked via the carboxymethylcellulose and wherein the peptide, the plurality of ligands, and the carboxymethylcellulose together form a water insoluble complex.

In a further aspect, the invention features a method for preparing a composition by providing a peptide and a plurality of ligands for the peptide; and combining the peptide and the plurality of ligands under conditions such that a water insoluble complex of the peptide and the plurality of ligands forms. The water insoluble complex formed may be further sterilized by, for example, heat, gamma irradiation or electron beam irradiation. Preferably, the water insoluble complex is formed using aseptic procedures, which can also be used as another means of sterilization.

In another aspect, the invention features a method for treating a subject for a condition treatable with a peptide by administering to the subject a composition which includes the peptide and a plurality of ligands for the peptide, the plurality of ligands being linked; wherein the peptide and the plurality of ligands together form a water insoluble complex. Preferably, the composition is sterilized by, for example, irradiation (e.g., gamma irradiation) or electron beam irradiation, prior to administration in vivo.

Other features and advantages of the invention will be apparent from the following detailed description, and from the claims.

BRIEF DESCRIPTION OF THE DRAWINGS

FIG. 1A depicts the composition of the invention where the plurality of ligands are linked directly to each other. FIG. 1B depicts the composition of the invention where the plurality of ligands are linked via a carrier macromolecule or a cross-linking agent.

FIG. 2A depicts the embodiment in which each of the plurality of ligands is positively charged and the carrier macromolecule is negatively charged. The plurality of ligands are linked indirectly via the carrier macromolecule. FIG. 2B depicts the embodiment in which each of the plurality of ligands is engineered to contain either a poly-L-lysine chain (having a net positive charge) or a poly-L-glutamate chain (having a net negative charge). The plurality of ligands are linked directly.

DETAILED DESCRIPTION OF THE INVENTION

Figure 1A:
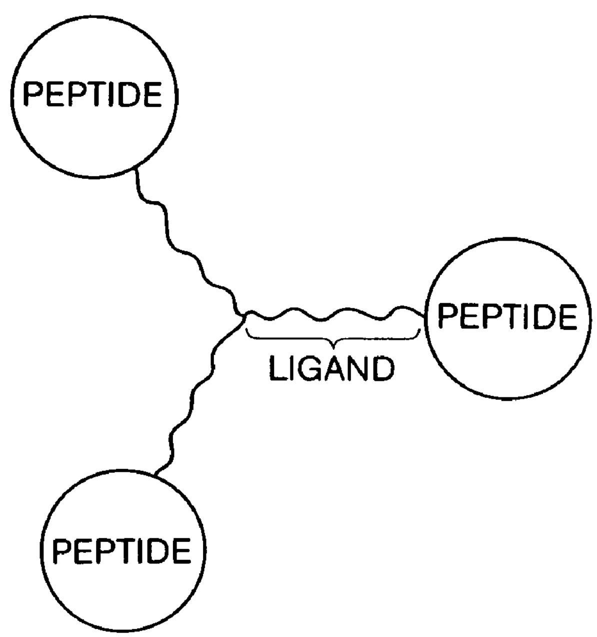
FIGS. 1A and 1B are schematic depictions of the compositions of the invention.
Figure 1B:
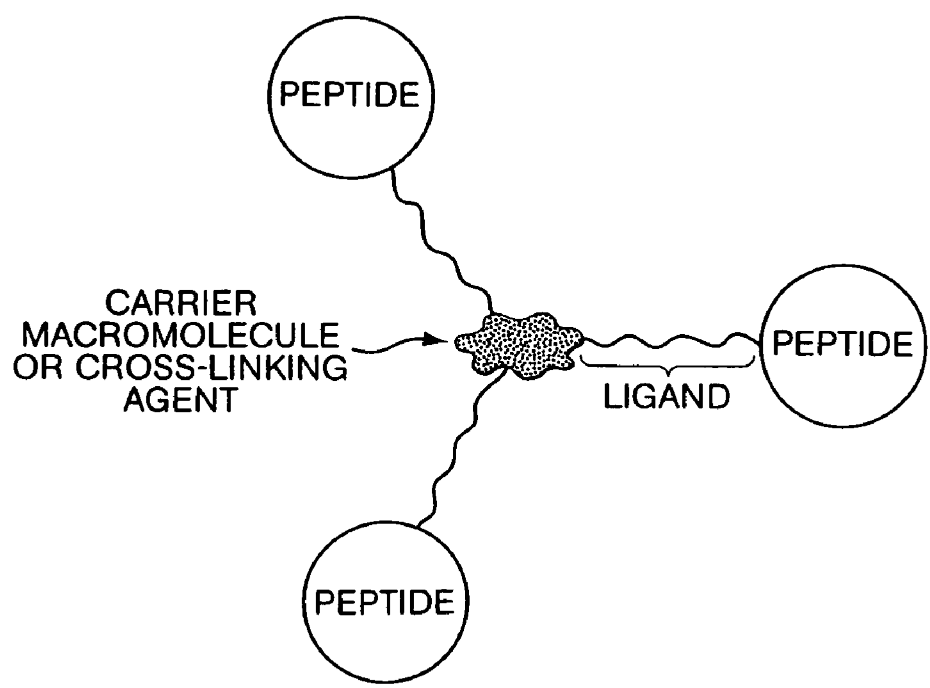
Figure 2A:
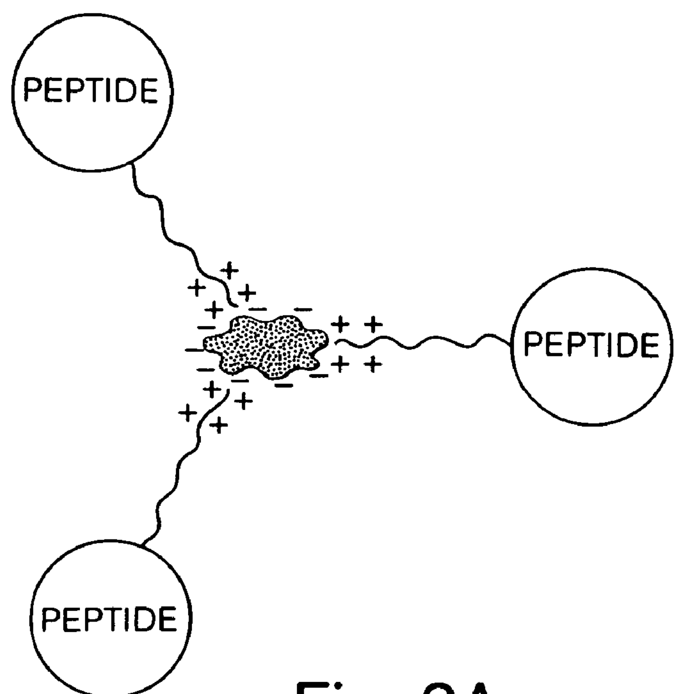
FIGS. 2A and 2B are schematic depictions of preferred embodiments of the invention.
Figure 2B:
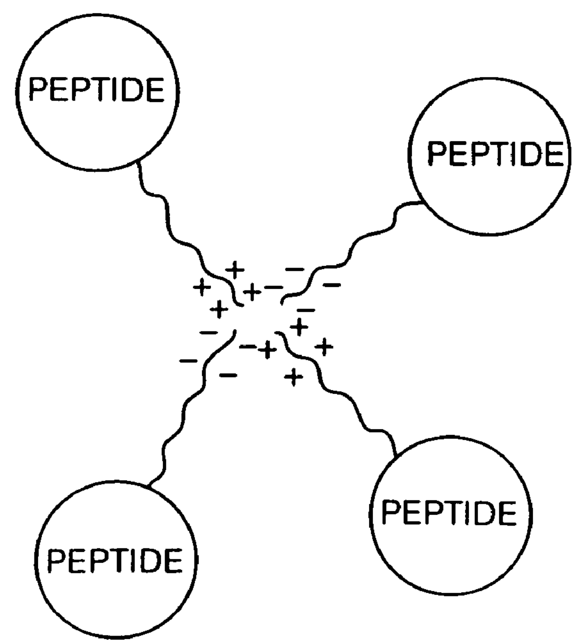

The present invention provides compositions comprising a stable solid, e.g., water insoluble, complex comprising a peptide or protein, preferably a pharmaceutically active peptide or protein, and a plurality of ligands for the peptide, that allow for sustained delivery of the peptide in vivo upon administration of the complex. The advantages of the compositions of the present invention include the ability for delivery of a peptide, either systemically or locally, for prolonged periods of time (e.g., one month) and the ability to load high concentrations of a peptide into the composition.

Accordingly, the invention features a composition which includes a peptide and a plurality of ligands for the peptide, the plurality of ligands being linked; wherein the peptide and the plurality of ligands together form a water insoluble complex.

As used herein, the terms "peptide" and "protein" are used interchangeably and are intended to include compounds comprising two or more amino acid residues linked by amide bonds. Such compounds can be natural biomolecules, such as proteins and peptide hormones, amino acid sequence variants of a natural biomolecule, or synthetic peptides. In one embodiment, the peptide includes any or all of the twenty natural L-amino acids. The peptide can also include one or more D-amino acid residues and/or one or more non-natural amino acid residues. Examples of peptides include insulin, erythropoietin (EPO), growth hormone, bradykinin, parathyroid hormone, adenocorticotrophic hormone, calcitonin, vasopressin, angiotensin, desmopressin, luteinizing hormone-releasing hormone (LHRH), somatostatin, glucagon, somatomedin, oxytocin, gastrin, secretin, melanocyte stimulating hormone, beta-endorphin, enkephalin, neurotensin, thyroid releasing hormone, macrophage stimulating factor, soluble CCR-5, tumor necrosis factor (TNF), growth hormone releasing factor (GRF), GRD, soluble TNF-9 receptor, interleukin, and other cytokines or cytokine mimetics.

The term "peptide" is further intended to encompass peptide analogues, peptide derivatives, and peptidomimetics that mimic the chemical structure of a peptide composed of naturally-occurring amino acids. The term "peptide analogue" as used herein is intended to include molecules that mimic the chemical structure of a peptide and retain the functional properties of the peptide. Examples of peptide analogues include peptides comprising one or more non-natural amino acids. The term "peptide derivative" as used herein is intended to include peptides in which an amino acid side chain, the peptide backbone, or the amino- or carboxyl-terminus has been derivatized (e.g., peptidic compounds with methylated amide linkages).

The term "peptidomimetic" as used herein is intended to include peptidic compounds in which the peptide backbone is substituted with one or more benzodiazepine molecules (see, e.g., James, G. L. et al. (1993) *Science* 260:1937-1942), "inverso" peptides in which all L-amino acids are substituted with the corresponding D-amino acids, "retro-inverso" peptides (see U.S. Pat. No. 4,522,752 by Sisto) in which the sequence of amino acids is reversed ("retro") and all L-amino acids are replaced with D-amino acids) "inverso") and other isosteres, such as peptide back-bone (i.e., amide bond) mimetics, including modifications of the amide nitrogen, the α-carbon, amide carbonyl, complete replacement of the amide bond, extensions, deletions or backbone crosslinks. Several peptide backbone modifications are known, including $\psi[CH_2S]$, $\psi[CH_2NH]$, $\psi[CSNH_2]$, $\psi[NHCO]$, $\psi[COCH_2]$, and ψ[(E) or (Z) CH═CH]. In the nomenclature used above, ψ indicates the absence of an amide bond. The structure that replaces the amide group is specified within the brackets. Other possible modifications include an N-alkyl (or aryl) substitution (ψ[CONR]), backbone crosslinking to construct lactams and other cyclic structures, and other derivatives including C-terminal hydroxymethyl derivatives, O-modified derivatives and N-terminally modified derivatives including substituted amides such as alkylamides and hydrazides.

As used herein, the term "pharmaceutically active peptide" is intended to include a peptide that exhibits a pharmacologic activity, either in its present form or upon processing in vivo (i.e., pharmaceutically active peptides include peptides with constitutive pharmacologic activity and peptides in a "pro-drug" form that have to be metabolized or processed in some way in vivo following administration in order to exhibit pharmacologic activity).

As used herein, the term "ligand" includes a molecule which has the ability to bind to or associate with a peptide. The ligand may be a peptidic molecule or a non-peptidic molecule. The ligand may be a natural ligand for the peptide (e.g., if the peptide is an LHRH antagonist or insulin, the ligand may be an LHRH receptor or an insulin receptor, respectively) or an artificially made ligand for the peptide, such as a fragment of a natural ligand. The ligands may be linked directly to each other via covalent interactions, via ionic interactions, via hydrophobic interactions, or a combination thereof. The ligands may also be linked indirectly, e.g., linked to a cross-linking agent or a carrier macromolecule, via covalent interactions, via ionic interactions, via hydrophobic interactions, or a combination thereof. Accordingly, the ligand also includes a region which will allow it to interact with another ligand or with a cross-linking agent or a carrier macromolecule.

As used herein, the term, "cross-linking agent" includes any agent that can be used to link the ligands of the invention. Preferred cross-linking agents are heterobifunctional cross-linkers, which can be used to link proteins in a stepwise manner. A wide variety of heterobifunctional cross-linkers are known in the art, including succinimidyl 4-(N-maleimidomethyl)cyclohexane-1-carboxylate (SMCC), m-Maleimidobenzoyl-N-hydroxysuccinimide ester (MBS); N-succinimidyl (4-iodoacetyl)aminobenzoate (SLAB), succinimidyl 4-(p-maleimidophenyl)butyrate (SMPB), 1-ethyl-3-(3-dimethylaminopropyl)carbodiimide hydrochloride (EDC); 4-succinimidyl-oxycarbonyl-a-methyl-a-(2-pyridyldithio)-tolune (SMPT), N-succinimidyl 3-(2-pyridyldithio)propionate (SPDP), succinimidyl 6-[3-(2-pyridyldithio)propionate]hexanoate (LC-SPDP).

As used herein, the term "carrier macromolecule" is intended to include any macromolecule that can be used to link the ligands of the invention. Preferably, the macromolecule has a molecular weight of at least 5 kDa, more preferably 10 kDa. The carrier macromolecule may comprise a single molecular species (e.g., a single type of polymer) or two or more different molecular species (e.g., a mixture of two or more types of polymers). The term carrier macromolecule includes anionic carrier macromolecules which are negatively charged, as well as cationic carrier macromolecules which are positively charged.

Examples of anionic carrier macromolecules include anionic polyalcohol derivatives or fragments thereof, anionic polysaccharides derivatives or fragments thereof, poly(allylamines), poly(vinylamines), poly(ethyleneimines), N-alkylated poly(allylamines), N-alkylated poly(vinylamines) or N-alkylated poly(ethyleneimines). Examples of specific anionic carrier macromolecules include carboxymethylcellulose, algin, alginate, anionic acetate polymers, anionic acrylic polymers, xantham gums, sodium starch glycolate, and fragments, derivatives and pharmaceutically acceptable salts thereof, as well as anionic carageenan derivatives, anionic polygalacturonic acid derivatives, and sulfated and sulfonated polystyrene derivatives. Examples of cationic polymers include poly-L-lysine, poly-L-arginine and other polymers of basic amino acids.

In a preferred embodiment, the composition provides sustained delivery of the peptide to a subject after the composition is administered to the subject. As used herein, the term "sustained delivery" is intended to refer to continual delivery of the peptide in vivo over a period of time following administration, preferably for at least several days (e.g., 2, 3, 4, 5, 6, 7, 8, 9, 10, or more days); one, two, three, or four weeks; or one, two, three, or four months. Sustained delivery of the peptide can be demonstrated by, for example, the continued therapeutic effect of the peptide over time (e.g., for an LHRH analogue, sustained delivery of the analogue can be demonstrated by continued suppression of testosterone synthesis over time). Alternatively, sustained delivery of the peptide may be demonstrated by detecting the presence of the peptide or a peptide metabolite in vivo over time.

Various aspects of the invention are described further in the following subsections.

I. Peptides

A variety of pharmaceutically active peptides may be used in the compositions of the invention, non-limiting examples of which include LHRH analogues, bradykinin and bradykinin analogues, parathyroid hormone, adenocorticotrophic hormone (ACTH), calcitonin, vasopressin and vasopressin analogues (e.g., 1-deamino-8-D-arginine vasopressin (DDAVP)), insulin, erythropoietin and erythropoietin peptide mimetics, growth hormone, parathyroid hormone, adenocorticotrophic hormone, calcitonin, angiotensin, desmopressin, luteinizing hormone-releasing hormone (LHRH), somatostatin, glucagon, somatomedin, oxytocin, gastrin, secretin, melanocyte stimulating hormone, beta-endorphin, enkephalin, neurotensin, thyroid releasing hormone, macrophage stimulating factor, CCR-5, tumor necrosis factor (TNF), growth hormone releasing factor (GRF), RGD, interleukin, and other cytokines or mimetics thereof. Analogues or derivatives of the aforementioned peptides may also be included in the compositions of the present invention.

Any size peptide may be suitable for use in the complex as long as the peptide has the ability to form a water-insoluble complex with the ligand (or with the ligand and the carrier macromolecule or cross-linking agent) upon combination of the peptide and the ligand (or the ligand and the carrier macromolecule or cross-linking agent).

The peptides to be used in the compositions of the present invention may be isolated from natural sources (e.g., purified by chromatography or crystallization), may be purchased, if they are commercially available, or they may be prepared by any suitable method for peptide synthesis (stepwise or convergent), including solution-phase and solid-phase chemical synthesis, or a combination of these approaches. Methods for chemically synthesizing peptides are well known in the art (see, e.g., Bodansky, M. *Principles of Peptide Synthesis*, Springer Verlag, Berlin (1993) and Grant, G. A (ed.). *Synthetic Peptides: A User's Guide*, W.H. Freeman and Company, New York (1992). Automated peptide synthesizers are commercially available (e.g., for small molecules).

In another embodiment, the peptides to be used in the compositions of the present invention are produced by recombinant DNA techniques. For example, the desired peptide can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector encoding the desired peptide can be transcribed and translated in vitro, for example, using T7 promoter regulatory sequences and T7 polymerase.

II. Ligands

Ligands that may be used in the present invention include any molecule which is capable of binding to or associating with a peptide. The ligand may be a peptidic molecule or a non-peptidic molecule. The ligand may be a natural ligand for the peptide (e.g., if the peptide is an LHRH antagonist or insulin, the ligand may be an LHRH receptor or an insulin receptor, respectively) or an artificially made ligand for the peptide, such as a fragment of a natural ligand, or a synthetic compound.

The ligands of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91: 11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

In one embodiment, the ligand is a peptidic compound. Accordingly, libraries comprising a multiplicity of potential peptidic ligands may be used to identify ligands that bind to a peptide of interest (i.e., the peptide to be used in the composition of the invention). A library comprising a multiplicity of peptidic ligands can be formed by any one of several methods known in the art. For example, in one embodiment, a multiplicity of nucleic acid molecules encoding a multiplicity of random peptidic ligands are synthesized and the nucleic acid molecules are introduced into a vector that allows for expression of the encoded peptidic ligand library. One example of such a library is an "external" library in which the peptidic ligand library is expressed on a surface protein of a host, such as a "phage display" library (see, e.g., Smith, G. P. (1985) *Science* 228:1315-1317; Parmley, S. F. and Smith, G. P. (1988) *Gene* 73:305-318; and Cwirla, S. et al. (1990) *Proc. Natl. Acad. Sci. USA* 87:6378-6382). As used herein, a "phage display" library is intended to refer to a library in which a multiplicity of peptidic ligands is displayed on the surface of a bacteriophage, such as a filamentous phage, preferably by fusion to a coat protein of the phage (e.g., the pIII protein or pVIII protein of filamentous phage). In phage-display methods, a multiplicity of nucleic acid molecules coding for peptidic ligands is synthesized and inserted into a phage vector to provide a recombinant vector. Suitable vectors for construction of phage display libraries include fUSE vectors, such as fUSE1, fUSE2, fUSE3 and fUSE5 (Smith and Scott (1993) *Methods Enzymol.* 217:228-257). Nucleic acid molecules can be synthesized according to methods known in the art (see, e.g., Cormack and Struhl, (1993) *Science* 262:244-248), including automated oligonucleotide synthesis. Following insertion of the nucleic acid molecules into the phage vector, the vector is introduced into a suitable host cell and the recombinant phage are extruded from the cell after a growth period. This results in a supernatant containing the recombinant phage which can then be used in screening assays with the target peptide of interest (i.e., the peptide to be used in the compositions of the invention).

Another example of a peptidic ligand library that may be used is a phagemid library described in, for example, U.S. Pat. No. 5,925,559, the contents of which are incorporated herein by reference.

Another example of a peptidic ligand library encoded by a multiplicity of nucleic acid molecules is an "internal" library, wherein the peptidic ligand members are expressed as fusions with an internal protein of a host (i.e., a non-surface protein) by inserting the nucleic acid molecules encoding the peptidic ligands into a gene encoding the internal protein. The internal protein may remain intracellular or may be secreted by, or recovered from, the host. Examples of internal proteins with which peptidic ligand library members can be fused include thioredoxin, staphnuclease, lac repressor (LacI), GAL4 and antibodies. An internal library vector is preferably a plasmid vector. In one example of an internal library, referred to as a two-hybrid system (see e.g., U.S. Pat. No. 5,283,173 by Field; Zervos et al. (1993) *Cell* 72:223-232; Madura et al. (1993) *J. Biol. Chem.* 268:12046-12054; Bartel et al. (1993) *Biotechniques* 14:920-924; and Iwabuchi et al. (1993) *Oncogene* 8:1693-1696), nucleic acid molecules encoding a multiplicity of peptidic ligands are inserted into a plasmid encoding the DNA binding domain of GAL4 (GAL4db) such that a library of GAL4db-peptide fusion proteins are encoded by the plasmid. Yeast cells (e.g., *Saccharomyces cerevisiae* YPB2 cells) are transformed simultaneously with the plasmid encoding the library of GAL4db-peptidic ligand fusion proteins and a second plasmid encoding a fusion protein composed of the target fused to the activation domain of GAL4 (GAL4ad). When the GAL4ad-target interacts with a GAL4db-peptide library member, the two domains of the GAL4 transcriptional activator protein are brought into sufficient proximity as to cause transcription of a reporter gene or a phenotypic marker gene whose expression is regulated by one or more GAL4 operators.

In another example of an internal library (see e.g., U.S. Pat. Nos. 5,270,181 and 5,292,646, both by McCoy), nucleic acid molecules encoding a multiplicity of peptidic ligands are inserted into a plasmid encoding thioredoxin such that a library of thioredoxin-peptidic ligand fusion proteins are encoded by the plasmid. The plasmid is introduced into a bacterial host cell where the thioredoxin-peptide fusion proteins are expressed cytoplasmically. The fusion proteins can be selectively released from the host cells (e.g., by osmotic shock or freeze-thaw procedures) and recovered for use in screening assays with the target peptide of interest (i.e., the peptide to be used in the compositions of the invention).

In yet another example of a library (described further in Cull, M. G. et al. (1992) *Proc. Natl. Acad. Sci. USA* 89:1865), nucleic acid molecules encoding a multiplicity of peptidic ligands are inserted into a gene encoding LacI to create a fusion gene encoding a fusion protein of LacI and the peptidic ligand library members. The plasmid encoding the fusion peptidic ligand library members is designed such that the fusion proteins binds to the plasmid (i.e., a plasmid encoding the LacI fusion proteins includes lac operator sequences to which LacI binds) such that the fusion proteins and the plasmids encoding them can be physically linked. Following expression of the fusion proteins in host cells, the cells are lysed to liberate the fusion protein and associated DNA, and the library is screened with an immobilized target (the peptide to be used in the compositions of the invention). Fusion proteins that bind to the target are recovered and the associated DNA is reintroduced into a cells for amplification and sequencing, thus allow for determination of the peptide sequence encoded by the DNA.

Alternative to forming a peptidic ligand library by synthesizing a multiplicity of nucleic acid molecules encoding the peptidic ligand library members, a multiplicity of peptidic ligands can be synthesized directly by standard chemical methods known in the art. For example, a multiplicity of peptidic ligands can be synthesized by "split synthesis" of peptidic ligands on solid supports (see, e.g., Lam, K. S. et al. (1993) *Bioorg. Med. Chem. Lett.* 3:419-424). Other exemplary chemical syntheses of peptidic ligand libraries include the pin method (see, e.g., Geysen, H. M. et al. (1984) *Proc. Natl. Acad. Sci. USA* 81:3998-4002); the tea-bag method (see, e.g., Houghten, R. A. et al. (1985) *Proc. Natl. Acad. Sci. USA* 82:5131-5135); coupling of amino acid mixtures (see, e.g., Tjoeng, F. S. et al. (1990) *Int. J. Pept. Protein Res.* 35:141-146; U.S. Pat. No. 5,010,175 to Rutter et al.); and synthesis of spatial arrays of compounds (see, e.g., Fodor, S. P. A. et al. (1991) *Science* 251:767). Peptidic ligand libraries formed by direct synthesis of the peptidic ligand library members preferably are bound to a solid support (e.g., a bead or pin, wherein each bead or pin is linked to a single peptide moiety) to facilitate separation of peptidic ligands that bind a target (the peptide to be used in the compositions of the invention) from candidate peptidic ligands that do not bind the target.

Once the ligand library has been formed, the target peptide of interest (i.e., the peptide to be used in the compositions of the invention) is screened with the ligand library to identify one or more library members that bind to the peptide. Ligands that bind the peptide (i.e., the peptide to be used in the compositions of the invention) can be selected according to known methods, such as biopanning of an immobilized target peptide with a phage display library. In one embodiment, a biotinylated target peptide is immobilized on a streptavidin-coated surface either before or after contacting the target peptide with a ligand library and unbound ligands are removed by washing. Ligand libraries bound to a solid support can be screened by, for example, contacting the ligands immobilized on the solid support with a labeled target peptide and detecting the labeled target peptide bound to library members or, alternatively, by releasing the ligands from the solid support and assaying the resulting solution (see, e.g., Ohlmeyer, M. H. J. et al. (1993) *Proc. Natl. Acad. Sci. USA* 90:10922:10926).

The selected library member or members preferably have a binding constant for binding to the target peptide of about 10 mM or less, about 1 mM or less, about 100 nM or less, about 10 nM or less, about 5 nM or less or about 1 nM or less. The selected library member or members preferably comprise 30 or fewer, 20 or fewer, 15 or fewer or ten or fewer amino acid residues.

The ligands (or sub-combinations thereof) may be linked directly to each other via covalent interactions, via ionic interactions, via hydrophobic interactions, or a combination thereof. The ligands (or sub-combinations thereof) may also be linked indirectly, e.g., linked to a cross-linking agent or a carrier macromolecule, via covalent interactions, via ionic interactions, via hydrophobic interactions, or a combination thereof. Accordingly, the ligand should also include a region which will allow it to interact with another ligand or with a cross-linking agent or a carrier macromolecule.

Thus, if necessary, following selection of one or more ligand peptide library members that bind to the target peptide (i.e., the peptide to be used in the compositions of the invention) the ligand may be modified such that it will be able to bind to other ligands or to carrier macromolecules or cross-linking agents. For example, the ligand may be fused to an amino acid sequence bearing a net electronic charge, e.g., a poly-cationic peptide, such as poly-L-lysine, or a poly-anionic peptide, such as poly-L-glutamate.

Moreover, the ligands of the present invention may be modified to contain one or more acidic or basic functional groups, such that they will be able to form pharmaceutically acceptable salts with pharmaceutically acceptable bases or acids, respectively, present on, for example, other ligands, carrier macromolecules or cross-linking agents. Suitable bases include a hydroxide, carbonate, or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Furthermore, the ligands of the present invention may be modified to contain biotin, such that they will be able to be cross-linked with a cross-linking agent such as avidin or streptavidin; or with another ligand containing avidin or streptavidin. It is also possible to modify the ligands of the present invention to contain avidin or streptavidin, such that they will be able to be cross-linked with a cross-linking agent such as biotin; or with another ligand containing biotin.

Peptidic ligands of the present invention may also be linked using heterobifunctional cross-linkers, which link proteins in a stepwise manner. A wide variety of heterobifunctional cross-linkers are known in the art and described herein.

III. Methods for Preparing the Compositions of the Invention

Another aspect of the invention pertains to methods for preparing the compositions of the invention. In one embodiment, the method includes providing a peptide and a plurality of ligands for the peptide; and combining the peptide and the plurality of ligands under conditions such that a water-insoluble complex (or a complex with limited solubility) of the peptide and the plurality of ligands forms.

In the situation where the composition also includes a carrier molecule or a cross-linking agent, the carrier molecule or the cross-linking agent may be combined with the peptide and the plurality of ligands under conditions such that a water-insoluble complex of the peptide, the plurality of ligands, and the carrier molecule or the cross-linking agent forms.

As used herein, the term "water-insoluble complex" is intended to refer to a physically and chemically stable complex that forms upon appropriate combining of a peptide and a plurality of ligands (or a peptide, a plurality of ligands, and a carrier macromolecule or a cross-linking agent) according to procedures described herein. This complex typically takes the form of a precipitate that is produced upon combining aqueous preparations of the peptide and the plurality of ligands (or the peptide, the plurality of ligands, and the carrier macromolecule or the cross-linking agent). Although not intending to be limited by mechanism, the formation of preferred water-insoluble complexes of the invention is thought to be mediated by (e.g., be mediated at least in part by) ionic interactions in situations where the peptide is cationic and each of the plurality of ligands (or carrier molecule or cross-linking agent) is anionic or vice versa. Additionally or alternatively, the formation of a water-insoluble complex of the invention may be mediated (e.g., be mediated at least in part by) hydrophobic interactions. Still further, formation of a water-insoluble complex of the invention may be mediated (e.g., be mediated at least in part by) covalent interactions. Description of the complex as being "water-insoluble" is intended to indicate that the complex does not substantially or readily dissolve in water, as indicated by its precipitation from aqueous solution. However, it should be understood that a "water-insoluble" complex of the invention may exhibit limited solubility in water either in vitro or in the aqueous physiological environment in vivo.

Typically, a solution of the peptide and a solution of the plurality of ligands are combined until a water-insoluble complex of the peptide and the plurality of ligands precipitates out of solution. The pH or ionic strength of the solution may be adjusted to optimize the precipitation of the complex. The pH should preferably be adjusted so that it is close to the physiologic pH. In certain embodiments, the solutions of the peptide and the plurality of ligands are aqueous solutions. Alternatively, if the peptide or the plurality of ligands (or both) are not substantially water soluble prior to combination the two, then the peptide and/or plurality of ligands can be dissolved in a water-miscible solvent, such as an alcohol (e.g., ethanol) prior to combining the two components of the complex. In another embodiment of the method of preparing the water-insoluble complex, the solution of the peptide and the solution of the plurality of ligands are combined and heated until a water-insoluble complex of the peptide and the plurality of ligands precipitates out of solution. The amounts of peptide and plurality of ligands necessary to achieve the water-insoluble complex may vary depending upon the particular peptide and ligand used, the particular solvent(s) used and/or the procedure used to achieve the complex. In certain embodiments, the ligand and the peptide are combined at a ratio of, for example, 0.5:1 to 0.1:1. In other embodiments, the ligand and the peptide used to form the complex are combined at a weight ratio of ligand:peptide of 0.9:1, 0.8:1, 0.7:1, 0.6:1, 0.5:1, 0.4:1, 0.3:1, 0.25:1, 0.2:1, 0.15:1, or 0.1:1. Ranges intermediate to the above recited values, e.g., 0.8:1 to 0.4:1, 0.6:1 to 0.2:1, or 0.5:1 to 0.1:1 are also intended to be part of this invention. For example, ranges of values using a combination of any of the above recited values as upper and/or lower limits are intended to be included.

In another embodiment, the peptide content of the complex is at least 45%, 50%, 55%, 60%, 65%, 70%, 75%, 80%, 85%, 90%, 95%, 96%, 97%, or 98% by weight. Ranges intermediate to the above recited values, e.g., at least about 50% to about 80%, at least about 60% to about 90%, or at least about 57% to about 82%, are also intended to be part of this invention. For example, ranges of values using a combination of any of the above recited values as upper and/or lower limits are intended to be included.

Once the peptide/ligand complex precipitates out of solution, the precipitate can be removed from the solution by means known in the art, such as filtration (e.g., through a 0.45 micron nylon membrane), centrifugation and the like. The recovered gel or paste can then be dried (e.g., in vacuum or in a 70° C. oven) and the solid can be milled or pulverized to a powder by means known in the art (e.g., hammer or ball milling, or in a fluid energy mill, or grinding in mortar and pestle). Alternatively, the gel or paste can be frozen and lyophilized to dryness. A concentration or dilution step or adjustment of the polarity, pH, or ionic strength can be introduced prior to or during isolation of the gel or past. The powder, gel, or paste form of the complex can be dispersed in a carrier solution to form a liquid suspension or semi-solid dispersion suitable for injection. Accordingly, in various embodiments, a pharmaceutical formulation of the invention is a lyophilized solid, a liquid suspension or a semi-solid dispersion.

The powder, gel, or paste form of the complex may be compressed into tablets or spheres, or extracted or compressed into a rod or disc. The powder, gel, or paste form of the complex may be in a crystalline amorphous or pseudocrystalline structure, or in a clathrate-like cylinder of hydration.

In another embodiment, the composition of the invention is a sterile formulation. For example, following formation of the water-insoluble complex, the complex can be sterilized, optimally by irradiation (e.g., gamma irradiation) or electron beam sterilization. Accordingly, the method of the invention for preparing a composition as described above can further comprise sterilizing the water-insoluble complex by gamma irradiation or electron beam irradiation. Alternatively, to prepare a sterile composition, the water-insoluble complex can be isolated using conventional sterile techniques (e.g., using sterile starting materials and carrying out the production process aseptically). Accordingly, in another embodiment of the method for preparing a composition as described above, the water-insoluble complex is formed using aseptic procedures.

Pharmaceutical formulations, including powders, liquid suspensions, semi-solid dispersions, lyophilized solids, and sterilized forms thereof (e.g., by gamma irradiation), prepared according to the methods of the invention, are also encompassed by the invention.

IV. Methods of Using the Compositions of the Invention

In another aspect, the invention features a method for treating a subject for a condition treatable with a peptide by administering to the subject a composition which includes the peptide and a plurality of ligands for the peptide, the plurality of ligands being linked (or which includes the peptide, the plurality of ligands for the peptide, and a carrier molecule or a cross-linking agent). Preferably, the composition is sterilized by, for example, gamma irradiation or electron beam irradiation, prior to administration in vivo.

As used herein, the term "subject" is intended to include warm-blooded animals, preferably mammals, most preferably humans.

As used herein, the term "administering to a subject" is intended to refer to dispensing, delivering or applying the compositions of the invention to a subject by any suitable route for delivery of the composition to the desired location in the subject, including delivery by either the parenteral or oral route, intramuscular injection, subcutaneous/intradermal injection, intravenous injection, buccal administration, transdermal delivery and administration by the rectal, colonic, vaginal, intranasal or respiratory tract route.

As used herein, the term "a condition treatable with a peptide" is intended to include diseases, disorders and other conditions in which administration of a peptide has a desired effect, e.g., a therapeutically beneficial effect. The disease, disorder, or other condition can be a local or a systemic disease, disorder, or other condition. Examples of conditions treatable with a peptide include central nervous system (CNS) disorders such as cognitive and neurodegenerative disorders, examples of which include, but are not limited to, Alzheimer's disease, dementias related to Alzheimer's disease (such as Pick's disease), Parkinson's and other Lewy diffuse body diseases, senile dementia, myasthenia gravis, Huntington's disease, Gilles de la Tourette's syndrome, multiple sclerosis, amyotrophic lateral sclerosis, progressive supranuclear palsy, epilepsy, and Jakob-Creutzfieldt disease; autonomic function disorders such as hypertension and sleep disorders, and neuropsychiatric disorders, such as depression, schizophrenia, schizoaffective disorder, korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), and bipolar affective neurological disorders, e.g., migraine and obesity. Further CNS-related disorders include, for example, those listed in the American Psychiatric Association's Diagnostic and Statistical manual of Mental Disorders (DSM), the most current version of which is incorporated herein by reference in its entirety.

Further examples of conditions treatable with a peptide include cardiovascular system disorders such as arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrillation, Jervell syndrome, Lange-Nielsen syndrome, long-QT syndrome, congestive heart failure, sinus node dysfunction, angina, heart failure, hypertension, atrial fibrillation, atrial flutter, dilated cardiomyopathy, idiopathic cardiomyopathy, myocardial infarction, coronary artery disease, coronary artery spasm, and arrhythmia.

Examples of conditions treatable with a peptide also include cellular proliferation, growth, differentiation, or migration disorders such as cancer, e.g., prostate cancer, ovarian cancer, endometriosis, uterine fibroids, breast cancer, polycystic ovary syndrome, carcinoma, sarcoma, or leukemia; benign prostatic hypertrophy; tumor angiogenesis and metastasis; skeletal dysplasia; hematopoietic and/or myeloproliferative disorders.

Additional examples of conditions treatable with a peptide include hormonal disorders, such as type I and type II diabetes mellitus, pituitary disorders (e.g., growth disorders), thyroid disorders (e.g., hypothyroidism or hyperthyroidism), and reproductive or fertility disorders (e.g., disorders which affect the organs of the reproductive system, e.g., the prostate gland, the uterus, or the vagina; disorders which involve an imbalance in the levels of a reproductive hormone in a subject; disorders affecting the ability of a subject to reproduce; and disorders affecting secondary sex characteristic development, e.g., adrenal hyperplasia).

Examples of conditions treatable with a peptide further include inflammatory or immune system disorders, such as viral infection, inflammatory bowel disease, ulcerative colitis, Crohn's disease, leukocyte adhesion deficiency II syndrome, peritonitis, chronic obstructive pulmonary disease, lung inflammation, asthma, acute appendicitis, septic shock, nephritis, amyloidosis, rheumatoid arthritis, chronic bronchitis, sarcoidosis, scleroderma, lupus, polymyositis, Reiter's syndrome, psoriasis, pelvic inflammatory disease, inflammatory breast disease, orbital inflammatory disease, immune deficiency disorders (e.g., HIV, common variable immunodeficiency, congenital X-linked infantile hypogammaglobulinemia, transient hypogammaglobulinemia, selective IgA deficiency, chronic mucocutaneous candidiasis, severe combined immunodeficiency), autoimmune disorders.

Conditions treatable with a peptide also include hematopoietic or thrombotic disorders, for example, disseminated intravascular coagulation, thromboembolic vascular disease, anemia, lymphoma, leukemia, neutrophilia, neutropenia, myeloproliferative disorders, thrombocytosis, thrombocytopenia, von Willebrand disease, and hemophilia.

Conditions treatable with a peptide further include gastrointestinal and digestive disorders, such as esophageal disorders such as atresia and fistulas, stenosis, achalasia, esophageal rings and webs, hiatal hernia, lacerations, esophagitis, diverticula, systemic sclerosis (scleroderma), varices, esophageal tumors such as squamous cell carcinomas and adenocarcinomas, stomach disorders such as diaphragmatic hernias, pyloric stenosis, dyspepsia, gastritis, acute gastric erosion and ulceration, peptic ulcers, stomach tumors such as carcinomas and sarcomas, small intestine disorders such as congenital atresia and stenosis, diverticula, Meckel's diverticulum, pancreatic rests, ischemic bowel disease, infective enterocolitis, Crohn's disease, tumors of the small intestine such as carcinomas and sarcomas, disorders of the colon such as malabsorption, obstructive lesions such as hernias, megacolon, diverticular disease, melanosis coli, ischemic injury, hemorrhoids, angiodysplasia of right colon, inflammations of the colon such as ulcerative colitis, and tumors of the colon such as polyps and sarcomas; as well as metabolic disorders (e.g., lysosomal storage disease, type II glycogenolysis, Fabry's disease, enzyme deficiencies, and inborn errors of metabolism); hepatic disorders and renal disorders (e.g., renal failure and glomerulonephritis).

Further examples of conditions treatable with a peptide include labor associated conditions such as premature labor or late labor.

The compositions of the invention can be administered to the subject by any route suitable for achieving the desired therapeutic result(s), although preferred routes of administration are parenteral routes, in particular intramuscular (i.m.) injection and subcutaneous/intradermal (s.c./i.d.) injection. Alternatively, the compositions of the invention can be administered to the subject orally. Other suitable parental routes include intravenous injection, buccal administration, transdermal delivery and administration by the rectal, vaginal, ophthalmic, intranasal or respiratory tract route (e.g., via inhalation, inspiration, or nebulization). For administration by inhalation, the compositions of the invention can be delivered in the form of an aerosol spray from a pressurized container or dispenser which contains a suitable propellant, e.g., a gas such as carbon dioxide, MFA, CFC, or a nebulizer.

It should be noted that when a composition that provides sustained delivery for weeks to months by the i.m or s.c./i.d. route is administered by an alternative route, there may not be sustained delivery of the peptide for an equivalent length of time due to clearance of the peptide by other physiological mechanisms (i.e., the dosage form may be cleared from the site of delivery such that prolonged therapeutic effects are not observed for time periods as long as those observed with i.m or s.c./i.d. injection).

One or more peptides may be administered to a subject at the same or a different rate to achieve a therapeutic or diagnostic result.

When administered to a subject for therapeutic purposes, the compositions of the invention contain a therapeutically effective amount of a peptide. A "therapeutically effective amount" refers to an amount effective, at dosages and for periods of time necessary, to achieve the desired result. A therapeutically effective amount of a peptide may vary according to factors such as the disease state, age, and weight of the individual, and the ability of the peptide to elicit a desired response in the subject. Dosage regimens may be adjusted to provide the optimum therapeutic response. A therapeutically effective amount is also one in which any toxic or detrimental effects of the peptide are outweighed by the therapeutically beneficial effects. A non-limiting range for a therapeutically effective amount of a peptide is 0.001 to 15 mg/kg. It is to be noted that dosage values may vary with the severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In another embodiment, the compositions of the invention may be used for diagnostic purposes. For example, the compositions of the invention may be used to deliver a labeled peptide-ligand complex at a side within a subject for detection of, for example, a tumor, a thrombus, or an amyloid plaque associated with Alzheimer's Disease.

V. Packaged Formulations Containing the Compositions of the Invention

In addition to compositions of peptides complexed with a plurality of ligands (or complexed with a plurality of ligands, and a carrier macromolecule or a cross-linking agent) the invention further encompasses packaged formulations containing such complexes and syringes containing such complexes. For example, the invention provides a packaged formulation for treating a subject for a condition treatable with a peptide, e.g., a pharmaceutically active peptide, comprising a water-insoluble complex of a peptide and a plurality of ligands (or a peptide, a plurality of ligands, and a carrier macromolecule or a cross-linking agent) packaged with instructions for using the water-insoluble complex for treating a subject for a condition treatable with a peptide. In another embodiment, the invention provides a syringe having a lumen, wherein a water-insoluble complex of a peptide and a plurality of ligands (or a peptide, a plurality of ligands, and a carrier macromolecule or a cross-linking agent) is included in the lumen.

Certain preferred embodiments of the invention are described below.

Peptide-Ligand-Carrier Macromolecule

In one embodiment, the ligand is a peptide comprising a binding sequence and a charged sequence. The binding sequence and the charged sequence can be connected directly, for example, via a peptide bond, or indirectly, for example, via an intervening peptide sequence or a nonpeptidic linking moiety. In one embodiment, the binding sequence and the charged sequence overlap, that is, the binding sequence and the charged sequence share one or more amino acid residues. The charged sequence can be any amino acid sequence which bears a net positive or negative charge under physiological conditions. Preferably, the charged sequence has a net polyanionic or polycationic charge at physiological pH. The binding sequence comprises two or more amino acid residues, preferably three or more residues, more preferably four or more residues and, most preferably five or more residues. In one embodiment, the binding sequence comprises from two to about twenty amino acid residues, more preferably from about five to about twelve residues, and, most preferably, from about five to about ten residues. The charged sequence preferably comprises from about two to about twenty amino acid residues, more preferably from about five to about twenty residues and most preferably from about five to about twelve residues.

In one embodiment, the charged sequence is a sequence which facilitates transport across cell membranes. For example, a variety of cationic sequences are known to serve as intracellular transport agents. Suitable examples of such sequences include the 11 residue protein transduction domain from the human immunodeficiency virus (HIV) TAT protein and similar sequences comprising multiple arginine residues, such as are described in WO 99/29721, WO 99/55899 and WO 99/10376, the teachings of each of which are hereby incorporated by reference in their entirety. Other suitable charged sequences include poly(arginine) and poly(d-arginine) sequences. Further suitable peptides include those described in, for example, Derossi et al., (1994) *J. Biol. Chem.* 269, 10444-10450; Lindgren et al., (2000) *Trends Pharmacol. Sci.* 21, 99-103; Ho et al., *Cancer Research* 61, 474-477 (2001); U.S. Pat. No. 5,888,762; U.S. Pat. No. 6,015,787; U.S. Pat. No. 5,846,743; U.S. Pat. No. 5,747,641; U.S. Pat. No. 5,804,604, the contents of each of which are incorporated herein by reference in their entirety.

In this embodiment, the ligand comprising a binding sequence and a charged sequence is associated, via the binding sequence, with a protein or peptide of interest, i.e., a therapeutic protein or peptide, and, via the charged sequence, to a charged carrier macromolecule, such as a charged polymer or polyelectrolyte. The carrier macromolecule will have, under physiological conditions, an ionic charge opposite in sign to that of the charged sequence and will interact electrostatically with the charged sequence. The ligand molecules and the carrier macromolecule, thus, serve to crosslink multiple protein molecules and form a complex having, at most, limited aqueous solubility under physiological conditions.

In another embodiment, the ligand is a non-peptidic compound which includes a binding domain and a charged domain. In this embodiment, the ligand can be any molecule which binds the protein with a sufficient binding constant. The charged domain can include one or more, preferably two or more, functional groups which bear an electric charge under physiological conditions, for example, anionic groups such as carboxylate, carbonate, phosphonate, sulfonate, phosphate, sulfate and sulfamate groups, and cationic groups, such as primary, secondary, tertiary and quaternary ammonium, phosphonium, sulfonium, guanidinium and iminium groups. Preferably, the charged domain has a net polycationic or polyanionic charge under physiological conditions. In one embodiment, the binding domain is non-peptidic and the charged domain is a peptide sequence, such as one of the charged sequences described above.

Peptide-Polyvalent Ligand

In another embodiment, the ligand is a multivalent peptidic compound. In this embodiment, each ligand molecule comprises two or more binding sequences which are directly or indirectly covalently connected. For example, the binding sequences can be connected via their N- or C-termini to a covalent linking group. The covalent linking group can be peptidic or non-peptidic. In one embodiment, the linking group comprises a linear peptide sequence with one binding sequence attached to its C-terminus and another binding domain attached at its N-terminus. In another embodiment, the linking group is a branched peptide sequence, such as a sequence which includes one or more amino acid residues having side chains to which an additional sequence can be connected, such as a lysine (—$NH_2$), glutamate (—C(O)OH) or aspartate (—C(O)OH) residue in which the indicated side chain functional group serves as the starting point for a branching peptide sequence. Such branched peptidic linking groups can link at least two and, preferably, three or more binding sequences.

The linking group can also be non-peptidic, for example, non-peptidic groups derived from a non-peptidic molecule having two or more functional groups which can react with the N-terminal amino group or the C-terminal carboxylate group of two or more binding sequences. Suitable difunctional linking groups include —NH—(CH2)n-NH—, and —C(O)—(CH2)n-C(O)—, where n is two or greater, preferably two to about twenty-four. Other suitable linking groups can be derived from, for example, known cross-linking agents, such as polyamines and polycarboxylic acids using methods known in the art. Such cross-linking agents include, but are not limited to, succinimidyl 4-(N-maleimidomethyl) cyclohexane-1-carboxylate (SMCC), m-Maleimidobenzoyl-N-hydroxysuccinimide ester (MBS); N-succinimidyl (4-iodoacetyl)aminobenzoate (SIAB), succinimidyl 4-(p-maleimidophenyl)butyrate (SMPB), 1-ethyl-3-(3-dimethylaminopropyl)carbodiimide hydrochloride (EDC); 4-succinimidyl-oxycarbonyl-a-methyl-a-(2-pyridyldithio)-tolune (SMPT), N-succinimidyl 3-(2-pyridyldithio)propionate (SPDP), succinimidyl 6-[3-(2-pyridyldithio) propionate]hexanoate (LC-SPDP).

Drug-Carrier Macromolecule

The present invention further provides a solid ionic complex comprising a therapeutically active drug having an ionic charge under physiological conditions and an ionic carrier macromolecule, as described above. For example, the drug can be any compound having therapeutic or diagnostic utility which includes one or more functional groups which bear an ionic charge under physiological conditions, such as one of the groups described above. Preferably, the drug is polycationic or polyanionic under physiological conditions. For example, in one embodiment, the drug includes one or more basic nitrogen atoms, and the carrier macromolecule is an anionic polymer, such as carboxymethylcellulose. The drug can be a peptidic compound, a non-peptidic compound or a compound having both non-peptidic and peptidic structural elements. For example, the drug can include a non-peptidic portion to which is attached, either directly or via a spacer group, a charged peptide sequence. The drug can also be a peptide or a peptide which is interrupted at one or more points by a non-peptidic spacer group. In this embodiment, the ligand includes a charged amino acid sequence. In drugs which include a charged amino acid sequence, the charged sequence can be any sequence which bears a net ionic charge under physiological conditions, and is, generally, a charged amino acid sequence as described above. Preferably, the charged sequence is a polycationic intracellular transport sequence, as described above.

In one embodiment, the therapeutically active drug is a small molecule. As used herein, the term "small molecule" includes peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The following examples, which further illustrate the invention, should not be construed as limiting. The contents of all references, patents and published patent applications cited throughout this application, as well as the Figures are hereby incorporated by reference.

EXAMPLES

Example 1

A peptide ligand to human growth hormone (hGH) is isolated by affinity screening of a peptide library, as is known in the art. The sequence of the ligand is determined using known methods and the ligand is synthesized with an additional ten amino acid residue cationic sequence at the N- or C-terminus of the ligand, to form a modified ligand. Human growth hormone and the modified ligand are combined in aqueous solution in the presence of carboxymethylcellulose, thereby precipitating a solid complex comprising hGH, the modified ligand and carboxymethylcellulose.

Example 2

The peptide ligand to hGH described in Example 1, is fused to a $Gly_{10}$ linker sequence at its amino terminus using standard peptide synthesis methods. The resulting $Gly_{10}$-ligand fusion peptide is then linked to the carboxyl groups of carboxymethyl cellulose via amide bonds, using synthetic methods known in the art. The resulting peptide-derivatized carboxymethyl cellulose is then combined in aqueous solution with hGH, and the resulting precipitate is isolated.

Example 3

The Gly10-ligand fusion peptide described in Example 2 is coupled at its N-terminus to 1,3,5-tris(2-carboxyethyl)benzene via amide bond formation, as is known in the art. The resulting tris(peptide) compound is then combined in solution with hGH, resulting in precipitation of a solid, which is collected by filtration.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A composition comprising:

(a) a plurality of peptide molecules;

(b) a plurality of ligand molecules for said peptide molecules, wherein one or more ligand molecules bind to each of said plurality of peptide molecules, each of said ligand molecules being positively charged; and (c) a negatively charged carrier macromolecule;

wherein said plurality of peptide molecules, said plurality of ligand molecules and said carrier macromolecule together form a water insoluble complex.

2. The composition of claim 1, wherein each of said plurality of ligand molecules is a peptidic compound.

3. The composition of claim 1, wherein each of said plurality of ligand molecules is a non-peptidic compound.

4. The composition of claim 1, wherein each of said plurality of peptide molecules is selected from the group consisting of insulin, erythropoietin, growth hormone, bradykinin, parathyroid hormone, adenocorticotrophic hormone, calcitonin, vasopressin, angiotensin, desmopressin, luteinizing hormone-releasing hormone, somatostatin, glucagon, somatomedin, oxytocin, gastrin, secretin, melanocyte stimulating hormone, beta-endorphin, enkephalin, neurotensin, thyroid releasing hormone, macrophage stimulating factor, CCR-5, tumor necrosis factor (TNF), growth hormone releasing factor (GRF), RGD, and interleukin.

5. The composition of claim 1, wherein the each of said plurality of peptide molecules is an LHRH analogue.

6. The composition of claim 1, wherein the composition provides sustained delivery of the peptide to a subject for at least one week after the composition is administered to the subject.

7. The composition of claim 1, wherein the composition provides sustained delivery of the peptide to a subject for at least two weeks after the composition is administered to the subject.

8. The composition of claim 1, wherein the composition provides sustained delivery of the peptide to a subject for at least four weeks after the composition is administered to the subject.

9. The composition of claim 1, wherein each of said plurality of peptide molecules is releasable in vivo in a pharmaceutically active form.

10. The composition of claim 1, wherein the carrier macromolecule is selected from the group consisting of poly (allylamine), poly(vinylamine), poly(ethyleneimine), N-alkylated poly(allylamine), N-alkylated poly(vinylamine) and N-alkylated poly(ethyleneimine).

11. The composition of claim 1, wherein the carrier macromolecule is carboxymethylcellulose.

12. The composition of claim 1, wherein each of said ligand molecules is a poly(arginine) molecule.

13. The composition of claim 1, wherein each of said ligand molecules is a poly(d-arginine) molecule.

14. The composition of claim 1, wherein each of said ligand molecules is a poly(lysine) molecule.

15. The composition of claim 1, wherein said ligand comprises a binding sequence and a charged sequence.

16. The composition of claim 15, wherein said binding sequence and said charged sequence overlap.

17. The composition of claim 15, wherein said charged sequence is a sequence that facilitates transport across a cell membrane.

18. A composition comprising:

(a) a plurality of peptide molecules;

(b) a plurality of ligand molecules for said peptide molecules, wherein one or more ligand molecules bind to each of said plurality of peptide molecules, each of said ligand molecules comprising a binding sequence and a positively charged sequence; and (c) a negatively charged carrier macromolecule;

wherein said plurality of peptide molecules, said plurality of ligand molecules and said carrier macromolecule together form a water insoluble complex.

19. The composition of claim 18, wherein said binding sequence and said charged sequence overlap.

20. A composition comprising:

(a) a plurality of peptide molecules;

(b) a plurality of ligand molecules for said peptide molecules, wherein one or more ligand molecules bind to each of said plurality of peptide molecules, each of said ligand molecules being positively charged; and (c) carboxymethylcellulose;

wherein said plurality of peptide molecules, said plurality of ligand molecules and said carboxymethylcellulose together form a water insoluble complex.

21. A composition comprising:

(a) a plurality of peptide molecules, wherein each of said plurality of peptide molecules is selected from the group consisting of insulin, erythropoietin, growth hormone, bradykinin, parathyroid hormone, adenocorticotrophic hormone, calcitonin, vasopressin, angiotensin, desmopressin, luteinizing hormone-releasing hormone, somatostatin, glucagon, somatomedin, oxytocin, gastrin, secretin, melanocyte stimulating hormone, beta-endorphin, enkephalin, neurotensin, thyroid releasing hormone, macrophage stimulating factor, CCR-5, tumor necrosis factor (TNF), growth hormone releasing factor (GRF), RGD, an LHRH analogue, and interleukin;

(b) a plurality of ligand molecules for said peptide molecules, wherein one or more ligand molecules bind to each of said plurality of peptide molecules, each of said ligand molecules being positively charged; and (c) a negatively charged carrier macromolecule;

wherein said plurality of peptide molecules, said plurality of ligand molecules and said carrier macromolecule together form a water insoluble complex.

22. A composition comprising:

(a) a plurality of peptide molecules, wherein each of said plurality of peptide molecules is selected from the group consisting of insulin, erythropoietin, growth hormone, bradykinin, parathyroid hormone, adenocorticotrophic hormone, calcitonin, vasopressin, angiotensin, desmopressin, luteinizing hormone-releasing hormone, somatostatin, glucagon, somatomedin, oxytocin, gastrin, secretin, melanocyte stimulating hormone, beta-endorphin, enkephalin, neurotensin, thyroid releasing hormone, macrophage stimulating factor, CCR-5, tumor necrosis factor (TNF), growth hormone releasing factor (GRF), RGD, an LHRH analogue, and interleukin;

(b) a plurality of ligand molecules for said peptide molecules, wherein one or more ligand molecules bind to each of said plurality of peptide molecules, each of said ligand molecules being positively charged; and (c) carboxymethylcellulose;

wherein said plurality of peptide molecules, said plurality of ligand molecules and said carboxymethylcellulose together form a water insoluble complex.

* * * * *